(12) United States Patent
McNicholas

(10) Patent No.: US 9,980,492 B2
(45) Date of Patent: May 29, 2018

(54) LURE USEFUL TO OBTAIN CENSUS ON LOCAL BUCK DEER AND IN DEER HUNTING

(76) Inventor: John Walter McNicholas, New Cumberland, WV (US)

( * ) Notice: Subject to any disclaimer, the term of this patent is extended or adjusted under 35 U.S.C. 154(b) by 112 days.

(21) Appl. No.: 13/592,310

(22) Filed: Aug. 22, 2012

(65) Prior Publication Data

US 2013/0067790 A1 Mar. 21, 2013

Related U.S. Application Data

(60) Provisional application No. 61/535,879, filed on Sep. 16, 2011.

(51) Int. Cl.
*A01N 63/02* (2006.01)

(52) U.S. Cl.
CPC .................................. *A01N 63/02* (2013.01)

(58) Field of Classification Search
None
See application file for complete search history.

(56) References Cited

U.S. PATENT DOCUMENTS

| 4,944,940 A * | 7/1990 | Christenson, II | 424/84 |
| 2012/0282315 A1 * | 11/2012 | Tate | 424/409 |

OTHER PUBLICATIONS

Backwood Bound Bulletin Board, how to make a homemade deer attractant or lure, Dec. 4, 2007.*
Forum posted to TradGang.com, topic: Smokey;s Preorbital Results after only 8 days, posted Sep. 18, 2010.*
West Virginia Scent Maker Carves a Niche, Oct. 7, 2009, WV Metronews.*

* cited by examiner

*Primary Examiner* — Mina Haghighatian
*Assistant Examiner* — Luke E Karpinski
(74) *Attorney, Agent, or Firm* — Price & Adams P.C.

(57) ABSTRACT

A deer lure and a method for making a deer lure that allows hunters and photographers to easily attract deer, primarily bucks, in specific locations for the purpose of collecting census data on the bucks. The lure is a pre-orbital gland lure where left and right pre-orbital glands are matched together to provide a total DNA of that specific family of deer.

3 Claims, 1 Drawing Sheet

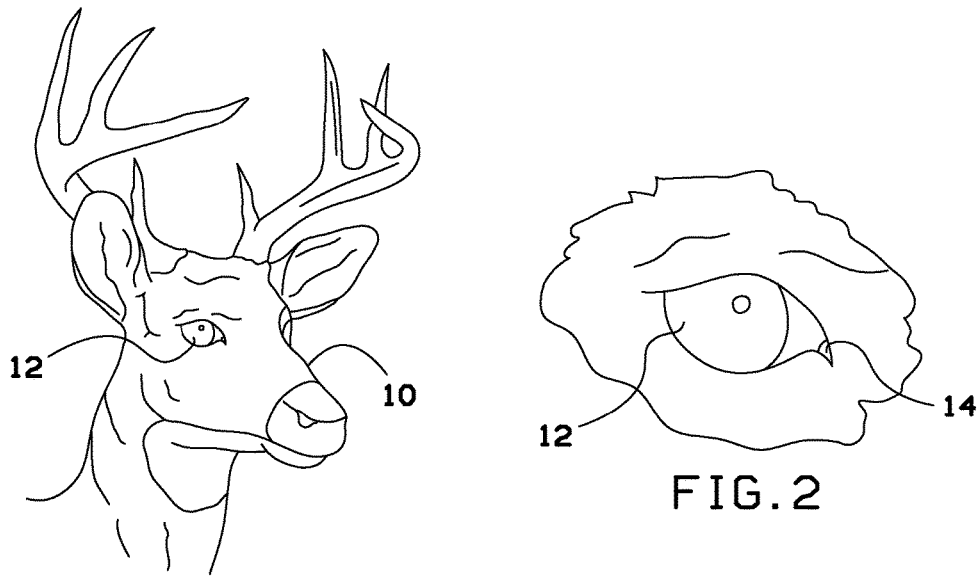
FIG.1
FIG.2
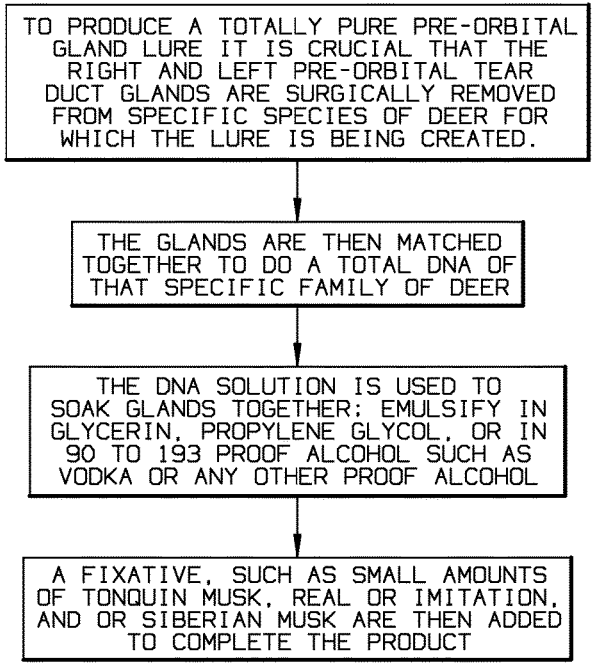
FIG.3

LURE USEFUL TO OBTAIN CENSUS ON LOCAL BUCK DEER AND IN DEER HUNTING

CROSS-REFERENCE TO RELATED APPLICATION

This application claims the benefit of priority of U.S. provisional application No. 61/535,879, filed Sep. 16, 2011, the contents of which are herein incorporated by reference.

BACKGROUND OF THE INVENTION

The present invention relates to deer lures and, more particularly, to a lure to be used to obtain census on local buck deer and in deer hunting.

Deer hunters and photographers often have a problem with collecting data on deer herds in specific locations. Creating an inventory of deer available to hunt or photograph using trail cameras has proven difficult.

Recent research has shown that the licking branch is the number one key to success when hunting a mock scrape. Bucks secrete a scent as a means of distinctly identifying themselves from the competition, helping them to understand their rank in the pecking order among the bucks in a given area. Bucks can keep tabs on one another by using licking branches and they do this year round. Bucks regularly visit licking branches and become aware when a new rival shows up when the licking branch has a scent of an unrecognized buck.

As can be seen, there is a need for a method and lure for obtaining census on local buck deer and in deer hunting, solving the problems that deer hunters and photographers had in the past of collecting data on their herds in specific locations.

SUMMARY OF THE INVENTION

In one aspect of the present invention, a deer lure comprises pre-orbital tear duct glands from both a left and right eye of a deer.

In another aspect of the present invention, a method for producing a deer lure comprises removing both left and right pre-orbital tear duct glands from a deer; soaking the glands together; and emulsifying the resulting mixture.

In a further aspect of the present invention, a method for obtaining census of bucks in a given area comprises applying a deer lure to a licking branch, the deer lure comprising pre-orbital tear duct glands from both a left and right eye of a deer; and obtaining an image of deer attracted to the licking branch by the deer lure.

These and other features, aspects and advantages of the present invention will become better understood with reference to the following drawings, description and claims.

BRIEF DESCRIPTION OF THE DRAWINGS

FIG. 1 is a perspective view of a head of a deer;

FIG. 2 is a detailed perspective view showing a pre-orbital tear duct gland of a deer; and FIG. 3 is a flow diagram, illustrating a method for producing a lure according to an exemplary embodiment of the present invention.

DETAILED DESCRIPTION OF THE INVENTION

The following detailed description is of the best currently contemplated modes of carrying out exemplary embodiments of the invention. The description is not to be taken in a limiting sense, but is made merely for the purpose of illustrating the general principles of the invention, since the scope of the invention is best defined by the appended claims.

Broadly, an embodiment of the present invention provides a deer lure and a method for making a deer lure. The lure allows hunters and photographers to easily attract deer, primarily bucks, in specific locations for the purpose of collecting census data on the bucks. The lure is a pre-orbital gland lure where left and right pre-orbital glands are matched together to provide a total DNA of that specific family of deer.

Referring now to FIGS. 1 and 2, a pre-orbital gland 14 from both the left and right eyes 12 of a deer 10 are used to produce the lure. By using both left and right pre-orbital glands matched together, a total DNA of that specific family of deer.

Referring now to FIG. 3, to produce a totally pure pre-orbital gland lure, both the left and right pre-orbital tear duct glands are surgically removed from the deer, the species being the same as that for which the lure is being created. The glands are then matched together to provide a total DNA of that specific family of deer. The glands can be soaked together in a DNA solution, emulsified in glycerin, propylene glycol, or in 90 to 193 proof alcohol, such as vodka or other proof alcohol. A fixative, such as small amounts of Tonquin Musk, real or imitation, and/or Siberian Musk, can be added.

The lure can be used, for example, beginning in July through October, to learn the big and small buck inventory in a particular hunting location. The lure can be used throughout the season, especially in the rut. An existing licking branch from a prior season or a new mock licking branch can be used to attract all the bucks in a given area. By applying a small amount directly to the branch, each buck will be curious about the new buck who is invading his territory. The lure can be reapplied as needed, typically on each visit to the location.

It should be understood, of course, that the foregoing relates to exemplary embodiments of the invention and that modifications may be made without departing from the spirit and scope of the invention as set forth in the following claims.

What is claimed is:

1. A method for producing a deer lure consisting essentially of the steps of:
   surgically removing only both left and right pre-orbital tear duct glands from a deer in a selected family of deer to the exclusion of any other product removed from any deer,
   matching the surgically removed pre-orbital tear duct gland from the right eye with the surgically removed pre-orbital tear duct gland from the left eye of the deer of the selected deer family,
   soaking together the surgically removed right eye and left eye pre-orbital tear duct glands from the deer to form a mixture purely of the right eye and left eye tear duct glands, said mixture being free of any other product removed from any deer, and
   thereafter combining the mixture of pure pre-orbital tear duct glands with an agent selected from the group consisting of glycerin, propylene glycol, and alcohol in the range of 90 to 193 proof.

2. The method of claim 1 which includes adding a fixative to the mixture of deer pre-orbital tear duct glands and agent.

3. The method of claim 2 which includes, selecting the fixative from the group consisting of Tonquin Musk and Siberian Musk.

\* \* \* \* \*